(12) United States Patent
Wicklein et al.

(10) Patent No.: US 12,369,865 B2
(45) Date of Patent: Jul. 29, 2025

(54) COMPUTER-IMPLEMENTED METHOD FOR PROVIDING AN OUTLINE OF A LESION IN DIGITAL BREAST TOMOSYNTHESIS

(71) Applicant: Siemens Healthineers AG, Forchheim (DE)

(72) Inventors: Julia Wicklein, Erlangen (DE); Ludwig Ritschl, Buttenheim (DE); Anna Jerebko, Paoli, PA (US)

(73) Assignee: SIEMENS HEALTHINEERS AG, Forchheim (DE)

( * ) Notice: Subject to any disclaimer, the term of this patent is extended or adjusted under 35 U.S.C. 154(b) by 279 days.

(21) Appl. No.: 17/881,860

(22) Filed: Aug. 5, 2022

(65) Prior Publication Data

US 2023/0053318 A1    Feb. 16, 2023

(30) Foreign Application Priority Data

Aug. 10, 2021 (EP) ..................... 21190576

(51) Int. Cl.
  *A61B 6/00* (2024.01)
  *A61B 6/02* (2006.01)
  *A61B 6/50* (2024.01)

(52) U.S. Cl.
  CPC .............. *A61B 6/025* (2013.01); *A61B 6/502* (2013.01); *G06T 2207/30068* (2013.01)

(58) Field of Classification Search
  CPC ................... A61B 6/025; A61B 6/502; G06T 2207/10112; G06T 2207/20081;

(Continued)

(56) References Cited

U.S. PATENT DOCUMENTS

| 10,010,302 B2 | 7/2018 | Ruth et al. |
| 2018/0158228 A1 | 6/2018 | Karssemeijer et al. |

(Continued)

FOREIGN PATENT DOCUMENTS

| EP | 3326535 A1 | 5/2018 |
| EP | 3797698 A1 | 3/2021 |

OTHER PUBLICATIONS

Giulia Rabottino, et al, "Performance evaluation of a region growing procedure for mammographic breast lesion identification", 2011, Computer Standards & Interfaces, vol. 33, Issue 2, pp. 128-135 (Year: 2011).*

(Continued)

*Primary Examiner* — David P Porta
*Assistant Examiner* — Miya Downing
(74) *Attorney, Agent, or Firm* — Harness, Dickey & Pierce, P.L.C.

(57) ABSTRACT

One or more example embodiments of the present invention relates to a computer-implemented method for providing an outline of a lesion in digital breast tomosynthesis includes receiving input data, wherein the input data comprises a reconstructed tomosynthesis volume dataset based on projection recordings, a virtual target marker within a lesion being in the tomosynthesis volume dataset; applying a trained function to at least a part of the tomosynthesis volume dataset to establish an outline enclosing the lesion, the part of the tomosynthesis volume dataset corresponding to a region surrounding the virtual target marker in the tomosynthesis volume dataset; and providing output data, wherein the output data is an outline of a two-dimensional area or a three-dimensional volume surrounding the target marker.

21 Claims, 6 Drawing Sheets

(58) Field of Classification Search
CPC . G06T 2207/20156; G06T 2207/30068; G06T 2207/30096; G06T 7/0012; G06T 7/11; G06T 7/187; G06T 2207/20101; G06T 2207/20084; G06V 10/82; G06V 2201/03; G06V 2201/07; G06V 2201/12
See application file for complete search history.

(56) References Cited

U.S. PATENT DOCUMENTS

| | | | |
|---|---|---|---|
| 2018/0271458 A1 | 9/2018 | Jerebko et al. | |
| 2021/0093275 A1 | 4/2021 | Hoernig et al. | |
| 2022/0036558 A1* | 2/2022 | Aum | G16H 30/40 |
| 2023/0091506 A1* | 3/2023 | Lotter | G16H 30/40 |
| | | | 382/131 |

OTHER PUBLICATIONS

Bick, Ulrich et al. "Image-guided breast biopsy and localisation: recommendations for information to women and referring physicians by the European Society of Breast Imaging." Insights into imaging vol. 11, 1 12. Feb. 5, 2020 (Year: 2020).*

Reiser et al: "Evaluation of a 3D lesion segmentation algorioothm on DBT and breast et images"; SPIE; PO Box 10 Bellingham WA 98227-0010; USA; vol. 7624, No. 2N-5; Mar. 9, 2010 (Mar. 9, 2010); pp. 1-7; XP040532972.

Zhang Jun et al: "Convolutional encoder-decoder for breast mass segmentation in digital breast tomosynthesis"; Progress in Biomedical Optics and Imaging; SPIE-International Society for Optical Engineering, Bellingham, WA, US; vol. 10575; Feb. 27, 2018 (Feb. 27, 2018); pp. 105752V-105752V; XP060101230; ISSN: 1605-7422; DOI: 10.1117/12.2295437.

Kim Seong Tae et al: "Combination of conspicuity improved synthetic mammograms and digital breast tomosynthesis: a promising approach for mass detection"; Progress in Biomedical Optics and Imaging; SPIE—International Society for Optical Engineering; Bellingham, WA, US; vol. 9414; Mar. 20, 2015 (Mar. 20, 2015); pp. 941419-941419; XP060052088; ISSN: 1605-7422; DOI: 10.1117/12.2081854; ISBN: 978-1-5106-0027-0.

Kronman, Achia et al; "Robust-Seed: seed-based segmentation improvement by optimisation"; Computer Methods in Biomechanics and Biomedical Engineering: Imaging & Visualization; vol. 6; No. 5; Mar. 6, 2017 (Mar. 6, 2017); pp. 564-572; DOI: 10.1080/21681163.2017.1298471.

Rahimeh Rouhi et al: "Benign and malignant breast tumors classification based on region growing and CNN segmentation"; Expert Systems With Applications; Oxford, GB; vol. 42; No. 3; pp. 990-1002, XP029095199, ISSN: 0957-4174, DOI:10.1016/J.ESWA.2014.09.020; Sektion 1; 2014.

* cited by examiner

COMPUTER-IMPLEMENTED METHOD FOR PROVIDING AN OUTLINE OF A LESION IN DIGITAL BREAST TOMOSYNTHESIS

CROSS-REFERENCE TO RELATED APPLICATION(S)

The present application claims priority under 35 U.S.C. § 119 to European Patent Application No. 21190576.5, filed Aug. 10, 2021, the entire contents of which are incorporated herein by reference.

FIELD

One or more example embodiments of the present invention relates to a computer-implemented method in digital breast tomosynthesis for providing an outline of a lesion, including where a target marker position within a lesion volume can be checked or improved based on the outline.

BACKGROUND

Digital Breast Tomosynthesis (DBT) allows for three-dimensional imaging of the breast. Multiple slices at different heights are reconstructed from several (e.g. 25) X-ray projections of the breast which are acquired at different angles over a limited angular range (e.g. 50°).

A major advantage of DBT towards conventional full-field digital mammography (FFDM) is the ability to resolve overlapping tissues. This is particularly valuable for identifying masses with speculated lesions in certain slices which, in FFDM, may be disguised by overlaid tissue structures and vessels from other slices. It is common practice to compute a synthetic mammogram from the acquired DBT data which can avoid the additional dose while maintaining the advantages of a 2D FFDM. Some mammography systems offer the possibility to calculate an additional rotating mammogram. This can consist of n reconstructed 2D synthetic mammograms of different scan angles, e.g P-8 ... P+8. The plurality of synthetic mammograms lies in an angular range. The synthetic mammograms can be tilted about an axis within the tomosynthesis volume.

Latest developments in terms of breast biopsy tend to use tomosynthesis imaging within the workflows, especially for targeting. Within the biopsy procedure, after the needle is inserted into the breast, a pre-fire image can be performed to check the relative position of the needle tip with respect to the lesion location. If the needle position is wrong, the needle must be removed, and a new target is set.

In conventional tomosynthesis, for example as part of a screening, AI-based CAD methods for the detection of lesions within the 3D layers can be used. The publication EP 3 326 535 A1 discloses a displaying system for displaying digital breast tomosynthesis (DBT) data. First and second DBT volume images of the left breast of a woman and first and second DBT volume images of the right breast of the woman are provided by an image providing unit. Moreover, for each DBT volume image a two-dimensional navigation image is provided by a navigation image providing unit, wherein a user is allowed to indicate a location in the navigation image by using a user interface, whereafter a CAD marker associated with the location is determined in a DBT volume image of a breast and a corresponding CAD marker, if present, is determined in another DBT volume image of the breast. Slices of these DBT volume images, which are associated with the CAD markers, are shown on a display.

AI-based CAD methods for the detection of lesions are based on deep learning methods, in which neural networks such as the U-Net are trained with a large number of data sets with known lesion positions (with image annotations). The trained networks are then able to generate a probability distribution of the tumor-relevant areas on unknown data sets. The resulting so-called probability maps can then be used to make the recognized areas visible in the synthetic 2D image. The publication U.S. Pat. No. 10,010,302 B2 discloses a 2D mammogram image which is synthesized from at least one of tomosynthesis projection images and/or the tomosynthesis reconstructed image data. In a simplest form, the mammogram may be synthesized by selecting one of the tomosynthesis projection images for display as a synthesized mammogram. Other methods of synthesizing a mammogram include re-projecting and filtering projection data and/or reconstructed data. The synthesized mammogram is advantageously displayed together with at least a portion of the reconstructed data to aid in review of the reconstructed data. This is done by different weighting of the individual layers based on the probability distributions and thus prevents disturbing overlays of tumor-affected areas.

The document US 2018 0 271 458 A1 describes a method for visualizing a region of interest inside an examination object into which an examination instrument has been introduced, and a tomosynthesis system for executing the method. Raw datasets are acquired from a number of lateral acquisition angles. A number of synthetic projections are calculated from the raw datasets. The synthetic projections are output in the form of an image sequence which represents the examination object in a rotating visualization.

The document EP 3 797 698 A1 describes a method for creating a synthetic mammogram based upon a dual energy tomosynthesis recording of an examination region. In an embodiment, the method includes making a low energy tomosynthesis recording with a first X-ray energy spectrum; making a high energy tomosynthesis recording with a second X-ray energy spectrum of a relatively higher energy compared with the first X-ray energy spectrum, wherein the examination region includes a contrast medium distribution; determining a subtraction volume based upon the high energy tomosynthesis recording and the low energy tomosynthesis recording; generating a three-dimensional probability map with a weighting factor per voxel based upon the subtraction volume; and creating a synthetic mammogram based upon the three-dimensional probability map.

SUMMARY

According to one or more example embodiments of the present invention incorrect needle positions are avoided/reduced and a method for providing an outline of a lesion in digital breast tomosynthesis supports a user with an improved view for checking a biopsy target position.

According to at least one example embodiment, a computer-implemented method for providing an outline of a lesion in digital breast tomosynthesis includes receiving input data, wherein the input data comprises a reconstructed tomosynthesis volume dataset based on projection recordings, a virtual target marker within a lesion being in the tomosynthesis volume dataset; applying a trained function to at least a part of the tomosynthesis volume dataset to establish an outline enclosing the lesion, the part of the tomosynthesis volume dataset corresponding to a region surrounding the virtual target marker in the tomosynthesis volume dataset; and providing output data, wherein the output data is an outline of a two-dimensional area or a three-dimensional volume surrounding the target marker.

According to at least one example embodiment, the virtual target marker defines a coordinate within the tomosynthesis volume data set for setting a biopsy target.

According to at least one example embodiment, the trained function comprises a segmentation method to generate the outline enclosing the lesion.

According to at least one example embodiment, the trained function comprises a region growing method to generate the outline enclosing the lesion.

According to at least one example embodiment, the method further includes displaying the target marker and the outline in conjunction with a display image dataset based on the projection recordings.

According to at least one example embodiment, the display image dataset comprises at least one slice of the tomosynthesis volume dataset.

According to at least one example embodiment, the display image dataset comprises a rotating mammogram.

According to at least one example embodiment, the rotating mammogram comprises a plurality of synthetic mammograms within an angular range tilting about an axis within a tomosynthesis volume associated with the tomosynthesis volume dataset.

According to at least one example embodiment, the two-dimensional area or the three-dimensional volume enclosed by the outline represents a volume of tumor-relevant tissue or a volume of the lesion.

According to at least one example embodiment, a color gradient depicts a distance between a location within the two-dimensional area or the three-dimensional volume enclosed by the outline and a center of the respective area or the respective volume.

According to at least one example embodiment, the method further includes performing a positioning check of the target marker with respect to the outline.

According to at least one example embodiment, a providing system for providing an outline of a lesion in digital breast tomosynthesis includes a first interface configured to receive input data, wherein the input data comprises a reconstructed tomosynthesis volume dataset based on projection recordings, a virtual target marker within a lesion being in the tomosynthesis volume dataset; a computation unit configured to apply a trained function to the input data to generate output data and to establish an outline enclosing the lesion, wherein the trained function is applied to at least a part of the tomosynthesis volume dataset corresponding to an area or a volume surrounding the virtual target marker in the tomosynthesis volume dataset; and a second interface configured to provide the output data, wherein the output data is an outline of a two-dimensional area or a three-dimensional volume surrounding the target marker.

According to at least one example embodiment, a non-transitory computer-readable medium comprises instructions which, when executed by a providing system, cause the providing system to carry out a method of one or more example embodiments.

According to at least one example embodiment, a digital breast tomosynthesis system comprises a providing system of one or more example embodiments.

One or more example embodiments of the present invention further relates to a providing system to carry out the method for providing an outline of a lesion in digital breast tomosynthesis according to one or more example embodiments of the present invention. The providing system can be a computer or any other computation unit, established locally or as a cloud-based service.

One or more example embodiments of the present invention further relates to a computer program comprising instructions which, when executed by a providing system, cause the providing system to carry out the method for providing an outline of a lesion in digital breast tomosynthesis according to one or more example embodiments of the present invention.

One or more example embodiments of the present invention further relates to a computer-readable medium comprising instructions which, when executed by a providing system, cause the providing system to carry out the method for providing an outline of a lesion in digital breast tomosynthesis according to one or more example embodiments of the present invention.

One or more example embodiments of the present invention further relates to a digital breast tomosynthesis system comprising the providing system according to one or more example embodiments of the present invention or for carrying out a method according to one or more example embodiments of the present invention.

BRIEF DESCRIPTION OF THE DRAWINGS

Further objects and advantages of the present invention will be apparent from the following description of example embodiments of the present invention as illustrated in the accompanying drawings, in which.

DETAILED DESCRIPTION

One or more example embodiments of the present invention relates to a computer-implemented method for providing an outline of a lesion in digital breast tomosynthesis, which comprises the following steps: receiving input data, wherein the input data comprises a reconstructed tomosynthesis volume dataset based on projection recordings, and a virtual target marker within a lesion in the tomosynthesis volume dataset, applying a trained function to at least a part of the tomosynthesis volume dataset corresponding to a region surrounding the virtual target marker in the tomosynthesis volume dataset to establish an outline enclosing the lesion, providing output data, wherein the output data is an outline of a two-dimensional area or a three-dimensional volume surrounding the target marker.

The method for providing an outline of a lesion in digital breast tomosynthesis can be used preferably in combination with a mammography system. The mammography system can comprise a biopsy unit for extracting a tissue sample or specimen. The virtual target marker can be set using a displaying unit, e.g. a (touch-)screen.

The input data can be received with a first interface. The input data comprises a reconstructed tomosynthesis volume dataset based on projection recordings. The tomosynthesis volume dataset can comprise DBT slices. The input data can be a three-dimensional mammography imaging dataset with a virtual target marker. The tomosynthesis volume dataset is reconstructed based upon the projection recordings. Multiple slices at different heights are reconstructed from several (e.g. 25) X-ray projections or projection recordings of the breast which are acquired at different angles over a limited angular range (e.g. 50°).

The input data further comprises a virtual target marker within a lesion in the tomosynthesis volume dataset. The virtual target marker can be set by a user. For example, a user assesses the tomosynthesis volume dataset, e.g. by viewing a plurality of slices. An AI-based CAD method can be used to determine masses and/or calcifications. The CAD method can determine masses based upon the projection recordings and/or the tomosynthesis dataset. The mass or the masses can be displayed in the tomosynthesis volume dataset to the user. The user can select a coordinate within the tomosynthesis volume dataset for setting the virtual target marker. Based on the user's experience and his/her knowledge, the position for the virtual target marker can be selected carefully. As alternative, the virtual target marker can be set automatically, e.g. based on the location of the mass.

A trained function is applied to at least a part of the tomosynthesis volume dataset. The part of the tomosynthesis volume dataset corresponds to a region surrounding the virtual target marker in the tomosynthesis volume dataset. By applying the trained function, an outline enclosing the lesion is established. The trained function can be applied to at least part of the tomosynthesis volume with a computation unit. The trained function is preferably trained by a machine learning algorithm. The trained function can be a common or known algorithm for image processing. Therefore, a training can be omitted. The trained function is applied to at least a part of the tomosynthesis volume dataset corresponding to a region surrounding the virtual target marker in the tomosynthesis volume dataset to establish an outline enclosing the lesion. The trained function is applied to at least a part of the tomosynthesis volume dataset. The part of the tomosynthesis volume dataset corresponds to a region surrounding the virtual target marker. The region can be an area or a volume surrounding the virtual target marker. The size of the region can be a predetermined size, e.g. corresponding to a radius around the virtual target marker or corresponding to a predetermined distance along the axes of the coordinate system. The predetermined distance can be different for different axes.

The trained function can be applied to planes (or areas) or volumes. In a preferred embodiment, the trained function can be applied to planes, or areas. The coordinate system can be a Cartesian coordinate system or any other suitable coordinate system. In case of a Cartesian coordinate system, the trained function can be applied to areas, e.g. in plane with the slice, especially in case the region is an area. In case the region is a volume, the trained function can be applied to areas, e.g. in plane with the slice and perpendicular to the plane of the slices. An area extending perpendicular to the plane of the slices can be a cross section through a stack of slices.

The output data can be provided with a second interface. The first interface and the second interface can be embodied as a common or combined physical interface, e.g. a network interface or a user interface. The output data is an outline of a two-dimensional area or a three-dimensional volume surrounding the target marker. The outline can be a boundary of the lesion or tumor-relevant tissue. The outline can show a volume or area which is affected by the lesion. The outline can depict a volume or an area which can be associated with the mass or the lesion. The outline can be provided in the form of a set of coordinates, e.g. within the tomosynthesis volume dataset. Regarding the virtual target marker, the position of the virtual target marker and the outline of the two-dimensional area or the three-dimensional volume can be compared. Based on the comparison, it is possible for the user to assess an accuracy or suitability of the position of the target marker for a successful biopsy procedure. The outline can be a measure of the extension of the lesion. The position of the target marker can be checked before inserting a needle into the breast. The position of the target marker can be checked without any invasive steps towards the body.

According to one or more example embodiments of the present invention, a new, alternative approach for a probability map for the special case of biopsy target tomosynthesis images is presented. Instead of a method based on deep learning with the corresponding training data, the probability map or affected volume or area can be based on the actual localization of a biopsy target or virtual target marker set by the radiologist within the DBT volume. A probability map can be based on the location of the lesion, e.g. x-/y- and z-coordinate directly given through the target, and on the extension of the lesion. A target area or target volume or target map for the biopsy can be based on the location of the lesion, x-/y- and z-coordinate directly given through the virtual target marker, and on the extension of the lesion. Additional machine learning can be performed on the area or volume surrounding the target position. E.g. a region growing approach can be used to enclose the total lesion outline or outlines. The output data comprises the outline. A target map can now be used for positioning check within an enhanced rotating or synthetic mammogram for biopsy procedures directly calculated out of tomosynthesis volume dataset, e.g. the tomo scout volume, and the corresponding target. A benefit of one or more example embodiments of the present invention can be to enable a so called tomo(synthesis) biopsy target positioning check directly after targeting, e.g. within a lesion-enhanced rotating or synthetic mammogram.

A biopsy procedure can be conducted as follows: After the patient is positioned properly and the breast is under compression, a DBT scout image is performed and displayed to the radiologist to set his/her virtual target marker into the area or the volume to be biopsied. This single position can return x-/y- and z-coordinate at a +/−1 mm target accuracy. Afterwards, the needle can be positioned and inserted into the breast. A check should be done to assure the right location of the set target, preferably before the needle is inserted into the breast and/or after insertion of the needle into the breast by another X-ray acquisition. Specimen imaging, clipping & control imaging, and decompression can follow.

According to one or more example embodiments of the present invention, the virtual target marker defines a coordinate within the tomosynthesis volume data set for setting a biopsy target. The target marker is a virtual marker, since the target marker is coordinate in the tomosynthesis volume dataset in contrast to a real marker within the breast tissue.

The biopsy needle can be controlled, e.g. by a control unit connected to a motion unit, using the coordinate or the virtual target marker.

According to one or more example embodiments of the present invention, the trained function comprises a segmentation method to generate the outline enclosing the lesion. A mass or a plurality of masses can be known, e.g. from AI-based CAD results. The trained function can use gradients or edges within the tomosynthesis volume dataset to determine the outline. A known segmentation method can be applied to the tomosynthesis volume dataset.

According to one or more example embodiments of the present invention, the trained function comprises a region growing method to generate the outline enclosing the lesion. Especially, a region growing method can be used to determine the outline based on the absorption of the tissue. Region growing is a special form of a segmentation method. Region growing is a region-based image segmentation method. It is also classified as a pixel-based image segmentation method since it involves the selection of initial seed points. For example, an initial seed point can be the virtual target marker. The region is then grown from the seed point to adjacent points depending on a region membership criterion. The criterion could be, for example, pixel intensity, or grayscale texture. Neighboring pixels of initial seed points are examined, and it is determined whether the pixel neighbors should be added to the region. The process is iterated on, in the same manner as general data clustering algorithms.

According to one or more example embodiments of the present invention, the method further comprises the step of displaying the target marker and the outline in conjunction with a display image dataset based on the projection recordings. The display image dataset can comprise a projection recording or a projection image. The display image dataset can show an overlay comprising the target marker and the outline. The target marker and the outline can be displayed as an overlay in a projection image or a plurality of projection images.

According to one or more example embodiments of the present invention, the display image dataset comprises a slice of the tomosynthesis volume dataset or, preferably, a plurality of slices of the tomosynthesis volume dataset. The outline as well as the target marker can be shown, e.g. as an overlay, in the display image dataset. In case the outline describes an area, the outline can be shown in a slice of the tomosynthesis volume dataset. In case the outline describes a volume, the outline can be shown in a plurality of slices of the tomosynthesis dataset.

According to one or more example embodiments of the present invention, the display image dataset comprises a rotating mammogram. The outline can be shown in a plurality of synthetic mammograms. The outline of a volume can be shown in a plurality of synthetic mammograms. By using the rotating view, the volume of the lesion or cross sections of the volume of the lesion can be viewed from different angles.

According to one or more example embodiments of the present invention, the rotating mammogram comprises a plurality of synthetic mammograms within an angular range tilting about an axis within the tomosynthesis volume. The plurality of synthetic mammograms lies in an angular range. The synthetic mammograms can be tilted about an axis within the tomosynthesis volume. Preferably, the axis intersects or comprises the virtual target marker. Preferably, the axis intersects the lesion, or the area or volume enclosed by the outline. For example, a slice image portion corresponding to a partial tissue region can be rotated. The slice image portion or region can be rotated over a range of discrete rotational angles for generating a set of rotation views. The rotation view can be displayed. A user can change the view from one angle to another, e.g. by using an interface. As a first view, the synthetic mammogram comprising the outline enclosing the largest area can be displayed.

According to one or more example embodiments of the present invention, the area or the volume enclosed by the outline represents a volume of tumor-relevant tissue or a volume of the lesion. The outline can depict a boundary of the lesion. The target map is based on the actual localization of a set biopsy target within the DBT volume.

According to one or more example embodiments of the present invention, a color gradient depicts the distance between a location within the area or the volume enclosed by the outline and the center of the area or the volume. The color gradient can be represented by gray values.

According to one or more example embodiments of the present invention, a positioning check of the target marker with respect to the outline is performed. A suggestion for an improved position of the virtual target marker can be provided, especially before inserting the needle into the breast. The suggestion can be accepted or declined by the user by a user input.

One or more example embodiments of the present invention further relates to a providing system for providing an outline of a lesion in digital breast tomosynthesis, comprising:
a first interface, configured for receiving input data, wherein the input data comprises a reconstructed tomosynthesis volume dataset based on projection recordings, and a virtual target marker within a lesion in the tomosynthesis volume dataset,
a computation unit, configured for applying a trained function to the input data, wherein the output data is generated, wherein the trained function is applied to at least a part of the tomosynthesis volume dataset corresponding to an area or a volume surrounding the virtual target marker in the tomosynthesis volume dataset to establish an outline enclosing the lesion,
a second interface, configured for providing output data, wherein the output data is an outline of a two-dimensional area or a three-dimensional volume surrounding the target marker.

The present invention will be further described in detail in conjunction with the accompanying drawings and embodiments. It should be understood that the particular embodiments described herein are only used to illustrate the present invention but not to limit the present invention.

Figure 1:
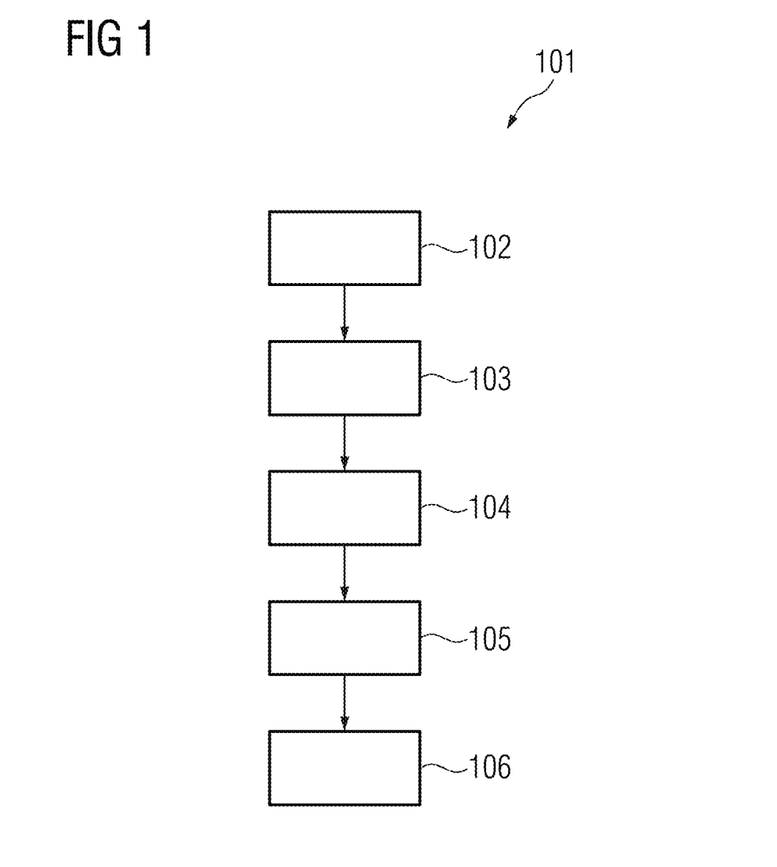
FIG. 1 is a method for providing an outline of a lesion in digital breast tomosynthesis according to one or more example embodiments of the present invention.

FIG. 1 shows a computer-implemented method 101 for providing an outline of a lesion in digital breast tomosynthesis. The method comprises the following steps: In a first step 102, input data is received, wherein the input data comprises a reconstructed tomosynthesis volume dataset based on projection recordings, and a virtual target marker within a lesion in the tomosynthesis volume dataset. In another step 103, a trained function is applied to at least a part of the tomosynthesis volume dataset corresponding to a region surrounding the virtual target marker in the tomosynthesis volume dataset to establish an outline enclosing the lesion. In another step 104, output data is provided, wherein the output data is an outline of a two-dimensional area or a three-dimensional volume surrounding the target marker.

The virtual target marker defines a coordinate within the tomosynthesis volume data set for setting a biopsy target. The trained function comprises a segmentation method to generate the outline enclosing the lesion. Preferably, the trained function comprises a region growing method to generate the outline enclosing the lesion.

The method further comprises the step of displaying 105 the target marker and the outline in conjunction with a display image dataset based on the projection recordings. The target marker and the outline can be displayed as an overlay in a projection image or a plurality of projection images. The display image data set comprises a slice of the tomosynthesis volume dataset or, preferably, a plurality of slices of the tomosynthesis volume dataset. In addition or as alternative, the display image dataset comprises a rotating mammogram, wherein the rotating mammogram comprises a plurality of synthetic mammograms within an angular range tilting about an axis within the tomosynthesis volume.

The area or the volume enclosed by the outline represents a volume of tumor-relevant tissue or a volume of the lesion. A color gradient depicts the distance between a location within the area or the volume enclosed by the outline and the center of the area or the volume. The color gradient can be represented by gray values.

In a further step, a positioning check 106 of the target marker with respect to the outline is performed, especially before inserting or without inserting a needle into the breast.

Figure 2:
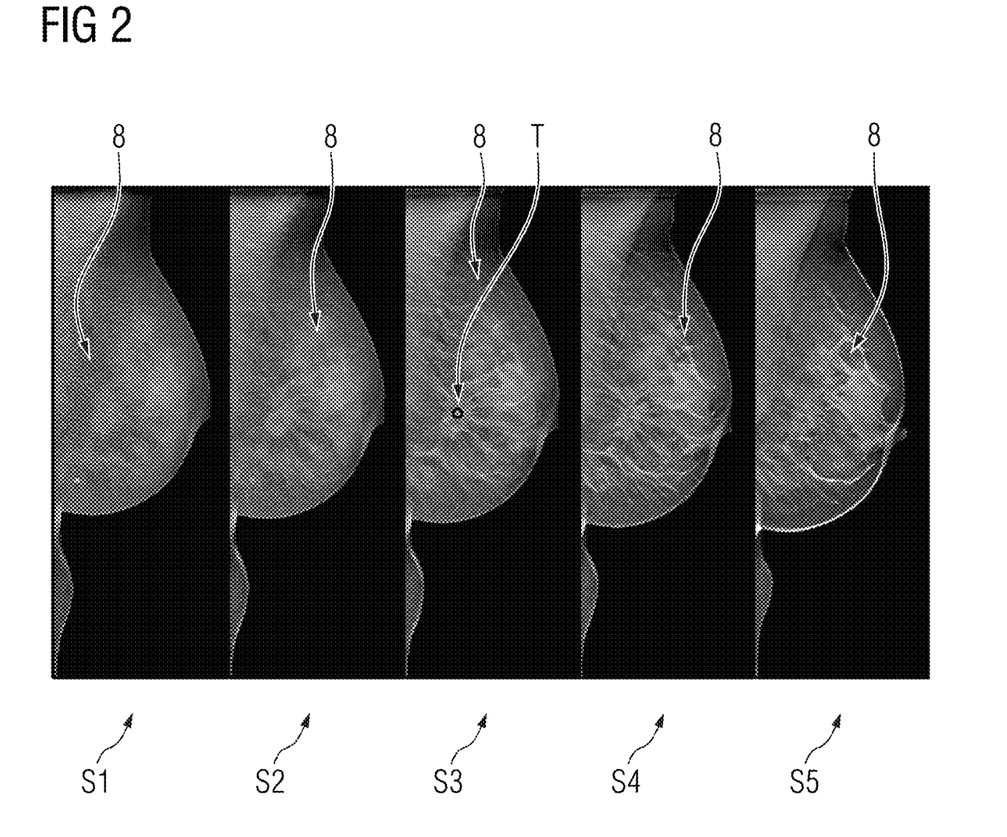
FIG. 2 is an illustration of a virtual target marker within a lesion in the tomosynthesis volume dataset according to one or more example embodiments of the present invention.

FIG. 2 shows an exemplary embodiment of a virtual target marker T within a lesion in the tomosynthesis volume dataset according to one or more example embodiments of the present invention. The tomosynthesis volume dataset comprises a plurality of (DBT) slices S1, . . . , S5. The slices show the tissue of the breast 8. In slice S3, the virtual target marker T is set at a target position. The tomosynthesis volume dataset can be a scout tomosynthesis volume data set.

Figure 3:
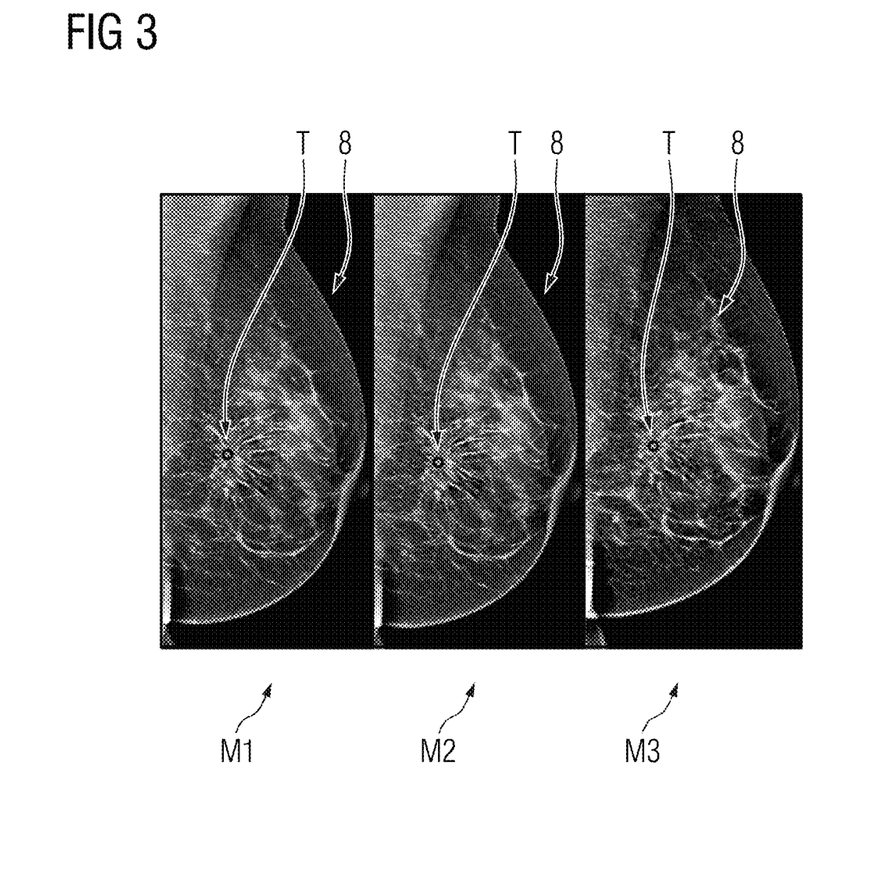
FIG. 3 is an illustration of a virtual target marker within a lesion in a lesion-enhanced rotating mammogram according to one or more example embodiments of the present invention.

FIG. 3 shows a virtual target marker within a lesion in a lesion-enhanced rotating mammogram according to one or more example embodiments of the present invention. The lesion-enhanced rotating mammogram comprises a plurality of views M1, M2, M3, e.g. P−8, P0 and P+8. In each view, the virtual target marker T is shown. The axis of rotation intersects the position of the virtual target marker T.

Figure 4:
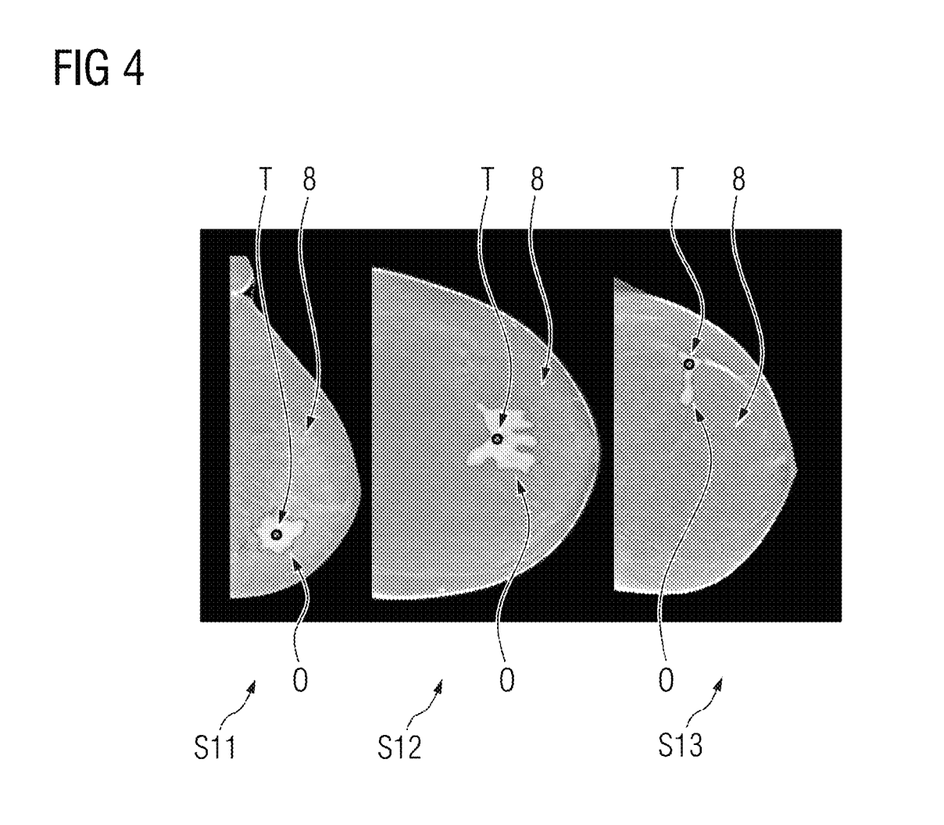
FIG. 4 is an illustration of a virtual target marker and an outline in the tomosynthesis volume dataset according to one or more example embodiments of the present invention.

FIG. 4 shows a virtual target marker T and an outline O in the tomosynthesis volume dataset according to one or more example embodiments of the present invention. In single (DBT) slices S11, S12, S13, e.g. referring to different tomosynthesis volume datasets, the virtual target marker T is shown for a lesion within the tomosynthesis volume dataset. In addition, the outline O is shown. The outline O was determined based on the region growing based lesion extension. A color gradient depicts the distance between a location within the area or the volume enclosed by the outline O and the center of the area or the volume. The color gradient can be represented by gray values.

Figure 5:
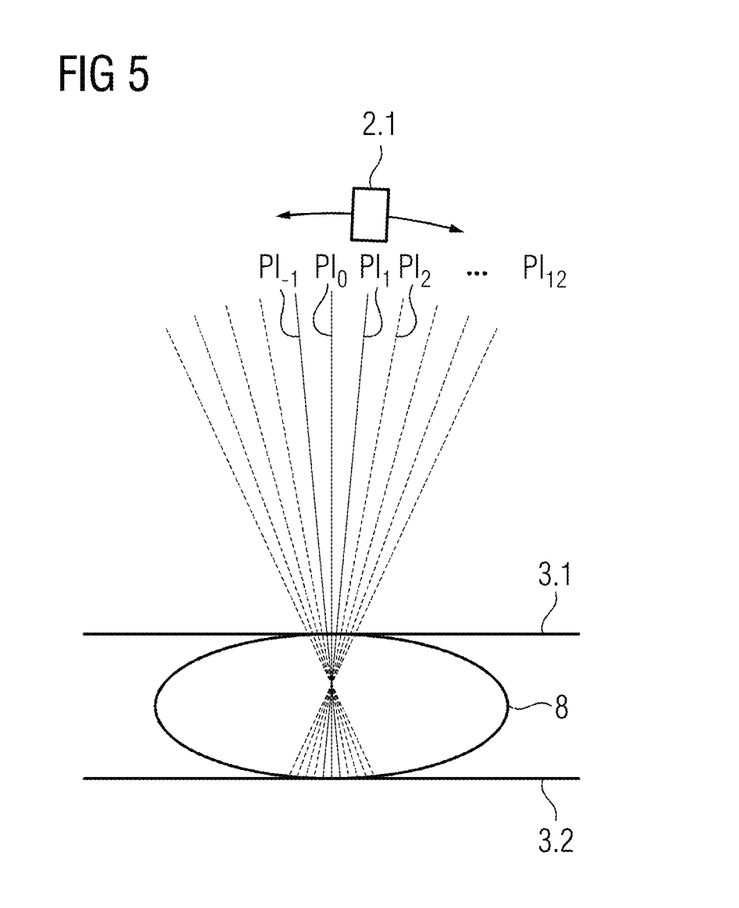
FIG. 5 is an illustration of a digital breast tomosynthesis system according to one or more example embodiments of the present invention.

FIG. 5 shows a digital breast tomosynthesis system according to one or more example embodiments of the present invention. For a tomosynthesis volume dataset, a plurality of projection recordings is recorded at a plurality of projection angles PI-1, 0, 1, 2, . . . , 12. The X-ray source 2.1 is thereby moved, in particular, along a radius about a point in the breast 8, whereby a projection recording is recorded at each of the projection angles PI-1, 0, 1, 2, . . . , 12. During the recording, the breast 8 of a patient is arranged as the examination object between an upper compression element 3.1 and a lower compression element 3.2.

Figure 6:
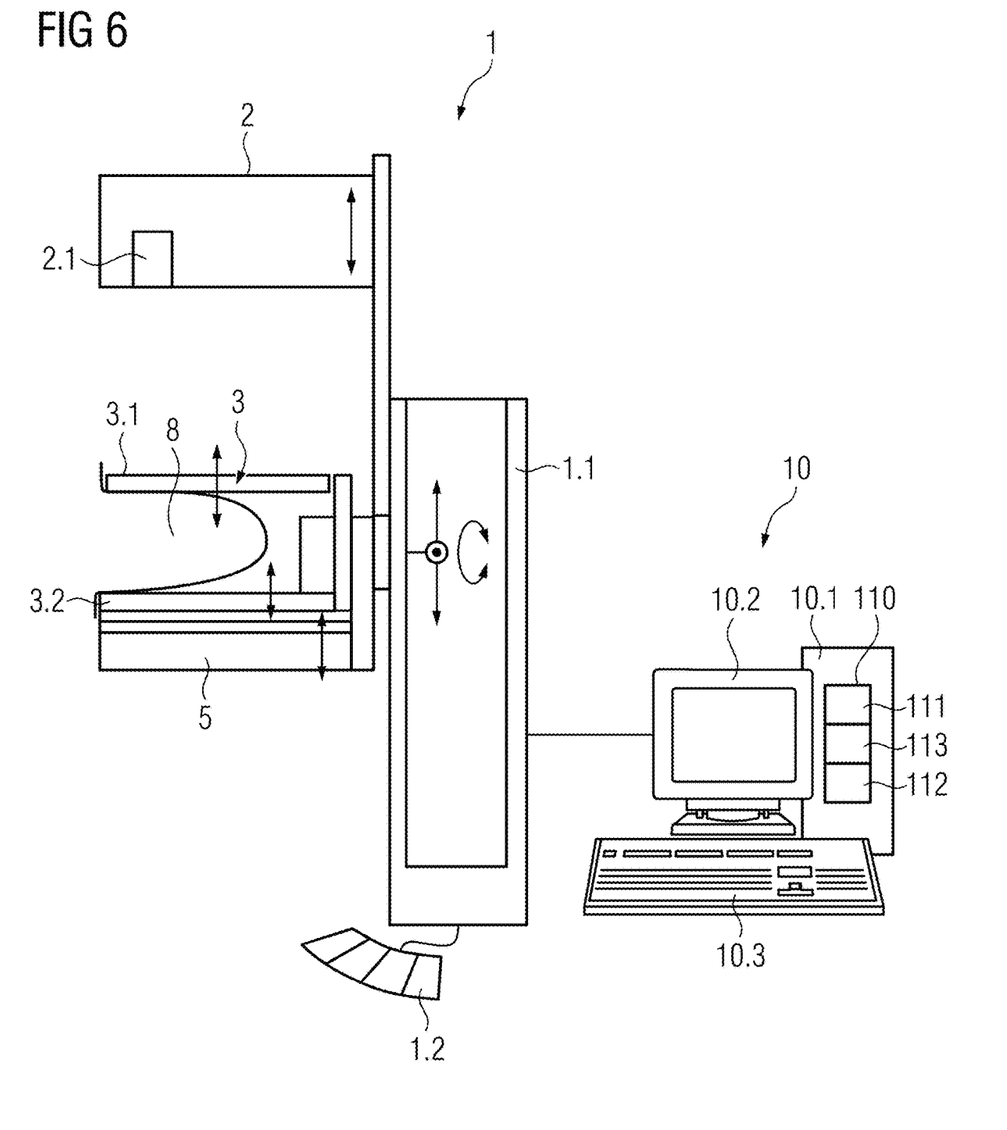
FIG. 6 is an illustration of a digital breast tomosynthesis system according to one or more example embodiments of the present invention.

FIG. 6 shows a digital breast tomosynthesis system 1 according to one or more example embodiments of the present invention. The digital breast tomosynthesis system 1 comprises a stand 1.1 on which the X-ray housing 2 having the X-ray source 2.1 and the X-ray detector 5 are arranged together with a compression unit 3. In particular, the X-ray housing 2 is mounted on the stand 1.1 to be rotatable relative to the stand 1.1 and the X-ray detector 5 and the compression unit 3. The compression unit 3 includes an upper compression element 3.1 and a lower compression element 3.2, between which the breast 8 of a patient is arranged. The digital breast tomosynthesis system 1 is connected to a data processing unit 10. The data processing unit 10 comprises at least one processor unit or computer unit 10.1, a display unit 10.2 and an input unit 10.3. A marking or setting of the virtual target marker can take place via the input unit. The computer unit 10.1 can comprise the providing unit 110. The providing unit 110 comprises the first interface 111, the second interface 113, and the computation unit 112. The digital breast tomosynthesis system 1 is at least partially controllable via a foot switch 1.2.

The providing system 110 for providing an outline of a lesion in digital breast tomosynthesis, comprises a first interface 111, configured for receiving input data, wherein the input data comprises a reconstructed tomosynthesis volume dataset based on projection recordings, and a virtual target marker within a lesion in the tomosynthesis volume dataset. The providing system 110 further comprises a computation unit 112, configured for applying a trained function to the input data, wherein the output data is generated, wherein the trained function is applied to at least a part of the tomosynthesis volume dataset corresponding to an area or a volume surrounding the virtual target marker in the tomosynthesis volume dataset to establish an outline enclosing the lesion. The providing system 110 further comprises a second interface 113, configured for providing output data, wherein the output data is an outline of a two-dimensional area or a three-dimensional volume surrounding the target marker.

Although some example embodiments of the present invention have been disclosed in the form of preferred embodiments and variations thereon, it will be understood that numerous additional modifications and variations could be made thereto without departing from the scope of example embodiments of the present invention. For the sake of clarity, it is to be understood that the use of "a" or "an" throughout this application does not exclude a plurality, and "comprising" does not exclude other steps or elements. The mention of a "unit", "module" or a "device" does not preclude the use of more than one unit or device.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'unit', 'interface' or the term 'controller' may be replaced with the term 'circuit.' The term 'module' and 'unit' may refer to, be part of, or include hardware, e.g., processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The present invention is not limited to the example embodiments described herein. Rather, other variants of the invention can also be derived herefrom by the person skilled in the art, without departing from the subject matter of the invention. In particular, it is furthermore possible to combine all the individual features described in connection with an example embodiment with one another in a different way also, without departing from the subject matter of the present invention.

We claim:

1. A computer-implemented method for providing an outline of a lesion in digital breast tomosynthesis, the method comprising:
receiving input data, wherein the input data comprises a reconstructed tomosynthesis volume dataset based on projection recordings, a virtual target marker within a lesion being in the reconstructed tomosynthesis volume dataset;
applying a trained function to at least a part of the reconstructed tomosynthesis volume dataset to establish an outline enclosing the lesion, the part of the reconstructed tomosynthesis volume dataset corresponding to a region surrounding the virtual target marker in the reconstructed tomosynthesis volume dataset; and
providing output data, wherein the output data is an outline of a two-dimensional area or a three-dimensional volume surrounding the virtual target marker.

2. The method according to claim 1, wherein the virtual target marker defines a coordinate within the reconstructed tomosynthesis volume dataset for setting a biopsy target.

3. The method according to claim 1, wherein the trained function comprises a segmentation method to generate the outline enclosing the lesion.

4. The method according to claim 1, wherein the trained function comprises a region growing method to generate the outline enclosing the lesion.

5. The method according to claim 1, further comprising:
displaying the virtual target marker and the outline in conjunction with a display image dataset based on the projection recordings.

6. The method according to claim 5, wherein the display image dataset comprises at least one slice of the reconstructed tomosynthesis volume dataset.

7. The method according to claim 5, wherein the display image dataset comprises a rotating mammogram.

8. The method according to claim 7, wherein the rotating mammogram comprises a plurality of synthetic mammograms within an angular range tilting about an axis within a tomosynthesis volume associated with the reconstructed tomosynthesis volume dataset.

9. The method according to claim 1, wherein the two-dimensional area or the three-dimensional volume enclosed by the outline represents a volume of tumor-relevant tissue or a volume of the lesion.

10. The method according to claim 1, wherein a color gradient depicts a distance between a location within the two-dimensional area or the three-dimensional volume enclosed by the outline and a center of the respective area or the respective volume.

11. The method according to claim 1, further comprising:
performing a positioning check of the virtual target marker with respect to the outline.

12. A providing system for providing an outline of a lesion in digital breast tomosynthesis, comprising:
a first interface configured to receive input data, wherein the input data comprises a reconstructed tomosynthesis volume dataset based on projection recordings, a virtual target marker within a lesion being in the reconstructed tomosynthesis volume dataset;
a computation unit configured to apply a trained function to the input data to generate output data and to establish an outline enclosing the lesion, wherein the trained function is applied to at least a part of the reconstructed tomosynthesis volume dataset corresponding to an area or a volume surrounding the virtual target marker in the reconstructed tomosynthesis volume dataset; and
a second interface configured to provide the output data, wherein the output data is an outline of a two-dimensional area or a three-dimensional volume surrounding the virtual target marker.

13. A non-transitory computer-readable medium comprising instructions which, when executed by a providing system, cause the providing system to carry out the method of claim 1.

14. A non-transitory computer-readable medium comprising instructions which, when executed by a providing system, cause the providing system to carry out the method of claim 2.

15. A digital breast tomosynthesis system comprising the providing system of claim 12.

16. A digital breast tomosynthesis system comprising a providing system configured to perform the method of claim 1.

17. The method according to claim 5, wherein a color gradient depicts a distance between a location within the two-dimensional area or the three-dimensional volume enclosed by the outline and a center of the respective area or the respective volume.

18. The method according to claim 6, wherein a color gradient depicts a distance between a location within the two-dimensional area or the three-dimensional volume enclosed by the outline and a center of the respective area or the respective volume.

19. The method according to claim 7, wherein a color gradient depicts a distance between a location within the two-dimensional area or the three-dimensional volume enclosed by the outline and a center of the respective area or the respective volume.

20. The method according to claim 2, wherein the trained function comprises a segmentation method to generate the outline enclosing the lesion.

21. The method of claim 11, further comprising:
providing a suggestion for an improved position of the virtual target marker based on the positioning check.

* * * * *